(12) United States Patent
Busch et al.

(10) Patent No.: US 6,774,368 B2
(45) Date of Patent: Aug. 10, 2004

(54) DISPERSIVE NEAR-INFRARED SPECTROMETER WITH AUTOMATIC WAVELENGTH CALIBRATION

(75) Inventors: Kenneth W. Busch, Waco, TX (US); Dennis H. Rabbe, Waco, TX (US)

(73) Assignee: Baylor University, Waco, TX (US)

( * ) Notice: Subject to any disclaimer, the term of this patent is extended or adjusted under 35 U.S.C. 154(b) by 59 days.

(21) Appl. No.: 10/093,584

(22) Filed: Mar. 8, 2002

(65) Prior Publication Data

US 2002/0175287 A1 Nov. 28, 2002

Related U.S. Application Data

(60) Provisional application No. 60/274,300, filed on Mar. 8, 2001.

(51) Int. Cl.[7] .................................................. G01J 3/44

(52) U.S. Cl. ............................ 250/339.09; 250/339.02; 356/51

(58) Field of Search ...................... 250/339.09, 339.02, 250/339.05, 328, 282, 288; 356/51, 73

(56) References Cited

U.S. PATENT DOCUMENTS

| | | | | |
|---|---|---|---|---|
| 5,040,889 A | * | 8/1991 | Keane .......................... | 356/51 |
| 5,394,237 A | * | 2/1995 | Chang et al. ................ | 356/328 |
| 6,067,156 A | * | 5/2000 | Slater et al. .................. | 356/301 |
| 6,411,373 B1 | * | 6/2002 | Garside et al. ................ | 356/39 |
| 6,452,177 B1 | * | 9/2002 | Feldman et al. ............ | 250/310 |
| 6,480,795 B1 | * | 11/2002 | Bossart et al. .............. | 702/104 |

OTHER PUBLICATIONS

Soyemi, et al, "Design of a modular, dispersive spectrometer for fundamental studies in NIR spectroscopy." Apr. 2001, 24–33, Spectroscopy.

Blank, et al, "Transfer of near–infrared multivariate calibrations without standards." Sep. 1, 1996, 2987–2995, Anal. Chem.

Wang, et al, "Multivariate Instrument Standardization." Dec. 1, 1991, 2750–2756, Anal Chem.

Lowry, et al, *"Determination of Wavelength Accuracy in the near–infrared spectral region based on NIST's infrared transmission wavelength standard SRM 1921."* Nov. 3, 2000, 450–455, Spectroscopic Techniques.

Busch, et al, *"Wavelength Calibration of a dispersive near–infrared spectrometer using trichloromethane as a calibration standard."* May 2000, 1321–1326, Applied Spectroscopy.

Busch, et al, *"Determination of the stray light levels in a dispersive near–infrared spectrometer with trichloromethane."* Aug. 2000, 1759–1766, Applied Spectroscopy.

Wiegenstein, et al, *"A virtual instrument approach for automation of temperature programmed desorption."* Oct. 1998, 3707–3708, Am Inst of Physics.

(List continued on next page.)

*Primary Examiner*—Constantine Hannaher
*Assistant Examiner*—Otilia Gabor
(74) *Attorney, Agent, or Firm*—Jackson Walker LLP

(57) ABSTRACT

The present invention is a dispersive, diffraction grating, NIR spectrometer that automatically calibrates the wavelength scale of the instrument without the need for external wavelength calibration materials. The invention results from the novel combination of: 1) a low power He—Ne laser at right angles to the source beam of the spectrometer; 2) a folding mirror to redirect the collimated laser beam so that it is parallel to the source beam; 3) the tendency of diffraction gratings to produce overlapping spectra of higher orders; 4) a "polka dot" beam splitter to redirect the majority of the laser beam toward the reference detector; 5) PbS detectors and 6) a software routine written in Lab VIEW that automatically corrects the wavelength scale of the instrument from the positions of the 632.8 nm laser line in the spectrum.

14 Claims, 10 Drawing Sheets

OTHER PUBLICATIONS

Koenig, et al, "A computer driven crystal spectrometer with charge coupled device detectors for x-ray spectroscopy of laser plasmas." Jun. 1997, 2387–2392, *Am Inst of Physics*.

Kirkman, et al, "Software." Jul. 16, 1991, 869–872, *Am Inst of Physics*.

Stryjewski, "Macintosh/lab VIEW based control and data acquisition system for a single photon counting fluorometer." Aug. 1991, 1921–1925, *Am Inst of Physics*.

de Viteri, Diamond "Virtual Instrument for flow–injection analysis with senor detection." Aug. 1994, 229–232, *Analytical Proceedings*.

Workman, et al, "Review of chemometrics applied to spectroscopy: 1985–95, Part 1." 1996, 74–124, *Applied Spectroscopy Reviews*.

Soyemi, "Design of data acquisition and analysis systems in near infrared spectroscopy: a virtual instrument approach." May 2000, *Dissertation–Doctor of Philosphy–Baylor U.*

FACSS 2000 Conference *Final Program Book of Abstracts*, Sep. 24–28, 2000, *FACSS National Office*.

Wells, "The LabVIEW student edition user's guide." *Prentice Hall, New Jersey*.

Griffiths, Haseth "Fourier transforms infrared spectrometry." 1986, *John Wiley & Sons, Inc. New York*.

Martens, et al, "Multivariate calibration." 1989, *John Wiley & Sons, Inc. New York*.

Burns, Ciurczak "Handbook of near–infrared analysis." 1992, *Marcel Dekker, Inc., New York*.

Workman and Coates "Multivariate Calibration Transfer The Importance of Standardizing Instrumentation." Nov./Dec. 1993, 36–42, Spectroscopy.

* cited by examiner

FIG. 5

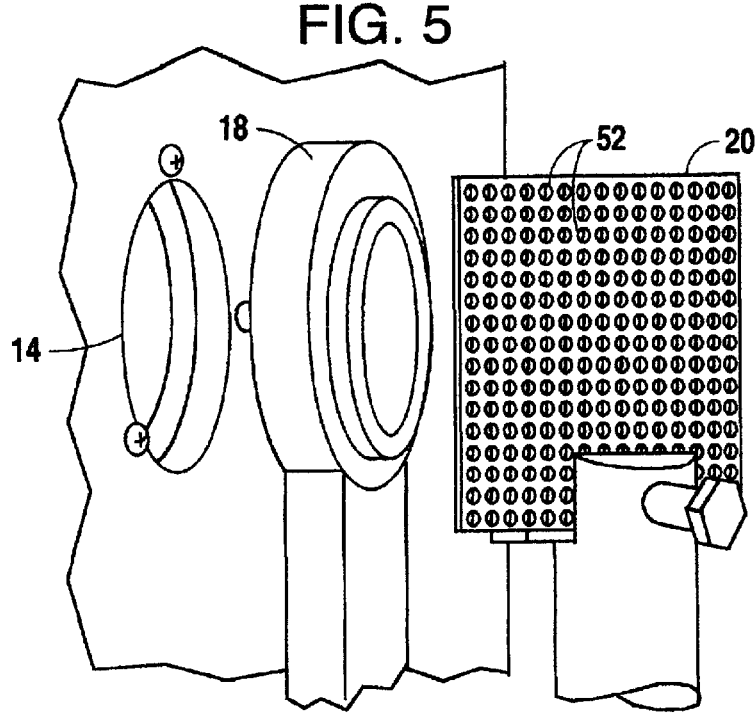

FIG. 6

$$\lambda_{CORRECTED} = (\lambda_{MEASURED} + \Delta) + \beta(\lambda_{MEASURED} - \lambda_{2nd\ ORDER})$$

$\underbrace{\phantom{(\lambda_{MEASURED} + \Delta)}}_{\text{SHIFTS SPECTRUM LEFT TO RIGHT}}$ $\underbrace{\phantom{\beta(\lambda_{MEASURED} - \lambda_{2nd\ ORDER})}}_{\text{CORRECTS DISPERSION}}$ $$\Delta = 1265.6 - \lambda_{2nd\ ORDER}$$

$$\beta = 1 - \alpha$$

$$\alpha = \frac{\lambda_{3rd\ ORDER} - \lambda_{2nd\ ORDER}}{632.8}$$

$\lambda_{2nd\ ORDER}$ = MEASURED $\lambda$ OF SECOND ORDER PEAK $\lambda_{3rd\ ORDER}$ = MEASURED $\lambda$ OF THIRD ORDER PEAK

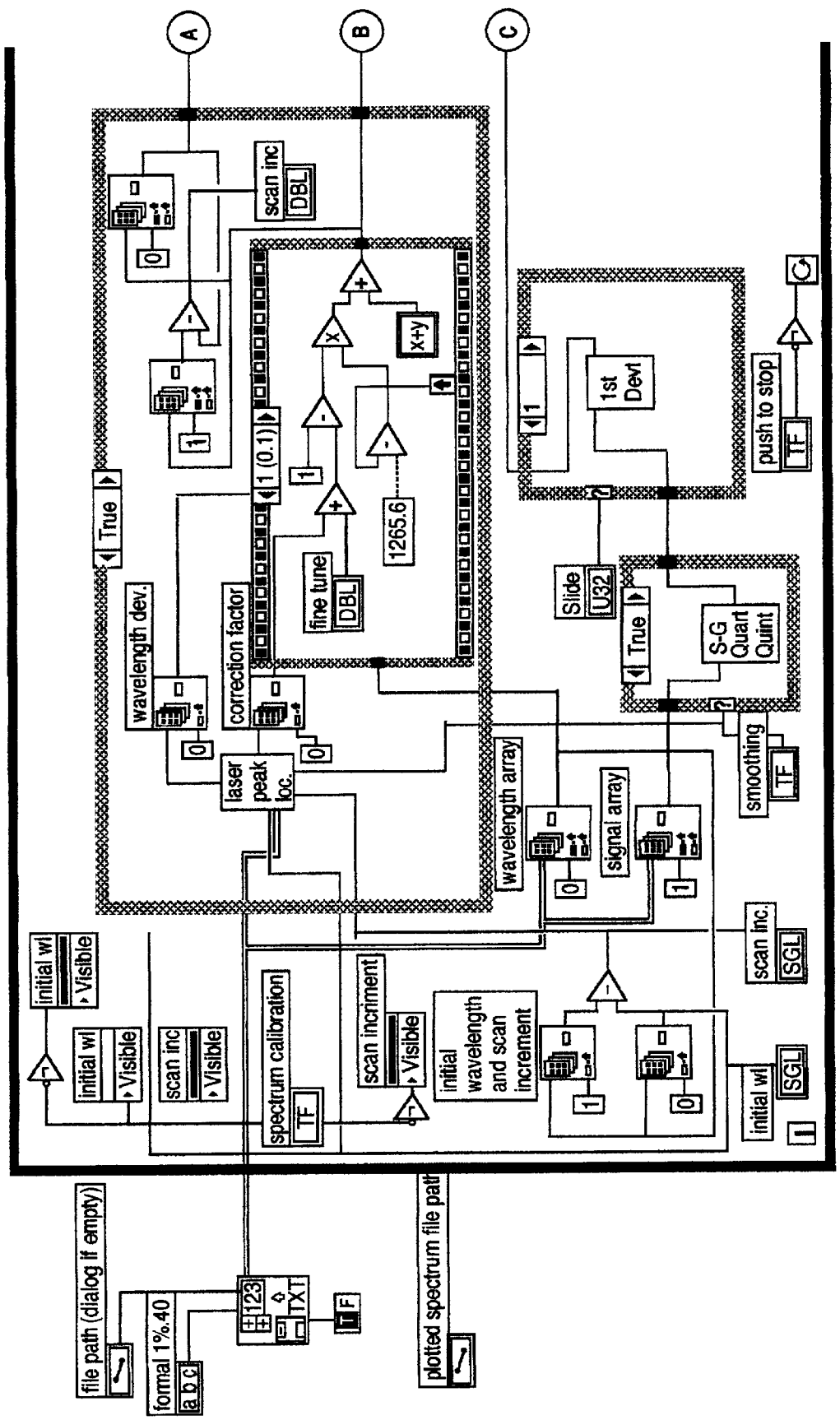
FIG. 8.1

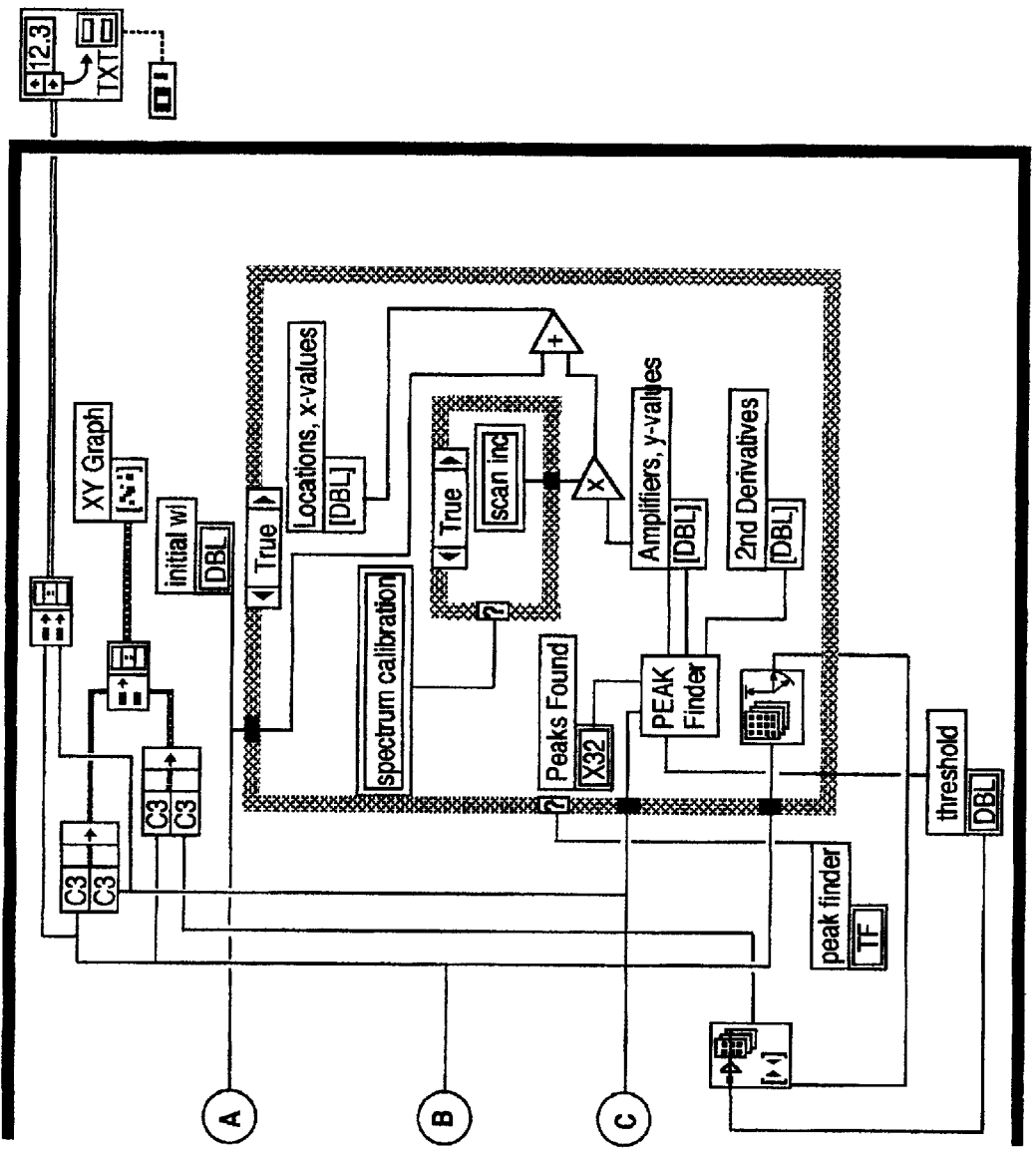
FIG. 8.2

DISPERSIVE NEAR-INFRARED SPECTROMETER WITH AUTOMATIC WAVELENGTH CALIBRATION

This application is based on and claims priority from provisional patent application, Serial No. 60/274,300, filed Mar. 8, 2001.

BACKGROUND OF THE INVENTION

The present invention relates to a Near-infrared (NIR) spectrometer with automatic wavelength calibration without the need of external calibrating. NIR spectroscopy is the measurement of the wavelength and intensity of the absorption of near-infrared light by a sample. Near-infrared light spans the 800 nm–2.5 micrometers ($\mu$m) range and is energetic enough to excite overtones and combinations of molecular vibrations to higher energy levels. NIR spectroscopy is typically used for quantitative measurement of organic functional groups, especially O—H, N—H, and C—H. Analyte detection limits are typically 0.1%.

NIR spectroscopy has been shown to be a powerful analytical tool for the analysis of agricultural products, food products, petroleum products, and pharmaceuticals products. Recently, NIR spectroscopy has been approved for the analysis of pharmaceutical products, a factor that is likely to dramatically extend the number of applications of the technique. In general, when NIR spectroscopy is combined with multivariate calibration procedures, the analytical methodology that results is rapid, accurate, and requires virtually no sample preparation.[1]

In conventional NIR spectroscopy, a multivariate statistical model is developed that attempts to correlate subtle changes in the NIR spectrum with known compositional changes determined by standard analytical technology. Once a robust model has been developed, NIR spectroscopic measurements can be substituted for the more time consuming, labor-intensive conventional analytical measurements.[2] To be completely useful, however, a model developed on one spectrometer in the laboratory should be capable of being used on different spectrometers without having to go through the model development all over again with the new instrument. To transfer a model from one spectrometer to another successfully, both instruments must ideally be identical.[3]

Many NIR spectrometers in use today employ dispersive systems that use diffraction grating monochromators. For these instruments, accurate wavelength calibration is important if the calibration models developed in the laboratory are to be used successfully on other instruments in the production environment. If the wavelength scales of different spectrometers are miscalibrated (as they inevitably are), problems with calibration transfer will occur.[4] Because of this, the standardization of NIR spectrometers has been pursued. The rational behind this being that if instruments are alike and remain stable enough, calibration transfer no longer becomes an analytical performance issue. Instrument standardization helps ensure that spectra produced from different instruments of the same design are essentially identical. In order to successfully carry out the various instrument standardization protocols, such as those suggested by Workman and Coates[5] and Wang, et al.[6], it is necessary to develop strategies that would accurately characterize all the instrumental variables of importance (i.e., wavelength and photometric accuracy, spectral bandwidth, and stray light). One way to avoid this problem is to use a wavelength standard to validate the wavelength scale of the spectrometer. Various wavelength standards exist.[7–10]

Recently, Busch and co-workers have proposed the use of trichloromethane as a substance with sharper, isolated absorption bands that are suitable for wavelength calibration of spectrometers in the NIR region.[11] The study of the use of trichloromethane as a wavelength standard showed that calibration of the wavelength scale of NIR instruments is absolutely essential, and a typical dispersive NIR spectrometer may be off by as much as 12 nm in the NIR region. Busch and co-workers have also assembled a research-grade NIR spectrometer that has been designed to allow the effect of various instrumental parameters on spectrometer performance to be studied in a systematic fashion. This is the same NIR spectrometer used to study the role of trichloromethane as a wavelength standard for NIR spectroscopy and to evaluate the stray light level in dispersive NIR spectrometers that has been designed to allow the effect of various instrumental parameters on spectrometer performance to be studied in a systematic fashion.[12] This disclosure describes a novel, dispersive, diffraction grating, NIR spectrometer that automatically calibrates the wavelength scale of the instrument without the need for external wavelength calibration materials.

SUMMARY OF THE INVENTION

In accordance with the above and related objects, the present invention is a dispersive, diffraction grating, NIR spectrometer that automatically calibrates the wavelength scale of the instrument without the need for external wavelength calibration materials. In a preferred embodiment, the present invention results from the novel combination of: 1) a low power He—Ne laser at right angles to the source beam of the spectrometer (FIGS. 2 and 3); 2) a folding mirror to redirect the collimated laser beam so that it is parallel to the source beam (see FIGS. 1 and 2); 3) the tendency of diffraction gratings to produce overlapping spectra of higher orders; 4) a "polka dot" beam splitter to redirect the majority of the laser beam toward the reference detector (FIGS. 3 and 4); 5) PbS detectors and 6) a software routine written in Lab VIEW that automatically corrects the wavelength scale of the instrument from the positions of the 632.8 nm laser line in the spectrum. Methods for making the aforesaid invention are included. In one particular embodiment, the claimed method includes obtaining an enhanced calibration set of NIR spectra by improving a dispersive, diffraction grating NIR spectrometer so that it automatically calibrates the wavelength scale of the spectrometer without the need for external wavelength calibration means. The improvement is further defined as obtaining and installing the novel parts as described above.

BRIEF DESCRIPTION OF THE DRAWINGS

FIG. 5 is a side view of the "Polka-dot" beam splitter which directs the majority of the laser beam toward the reference detector.

FIG. 6 shows the mathematical basis for the LabVIEW program that automatically calibrates the spectrometer.

FIG. 8 is a schematic diagram of the LabVIEW program that carries out the mathematical correction of the spectrum.

DETAILED DESCRIPTION OF THE PREFERRED EMBODIMENTS

Figure 1:
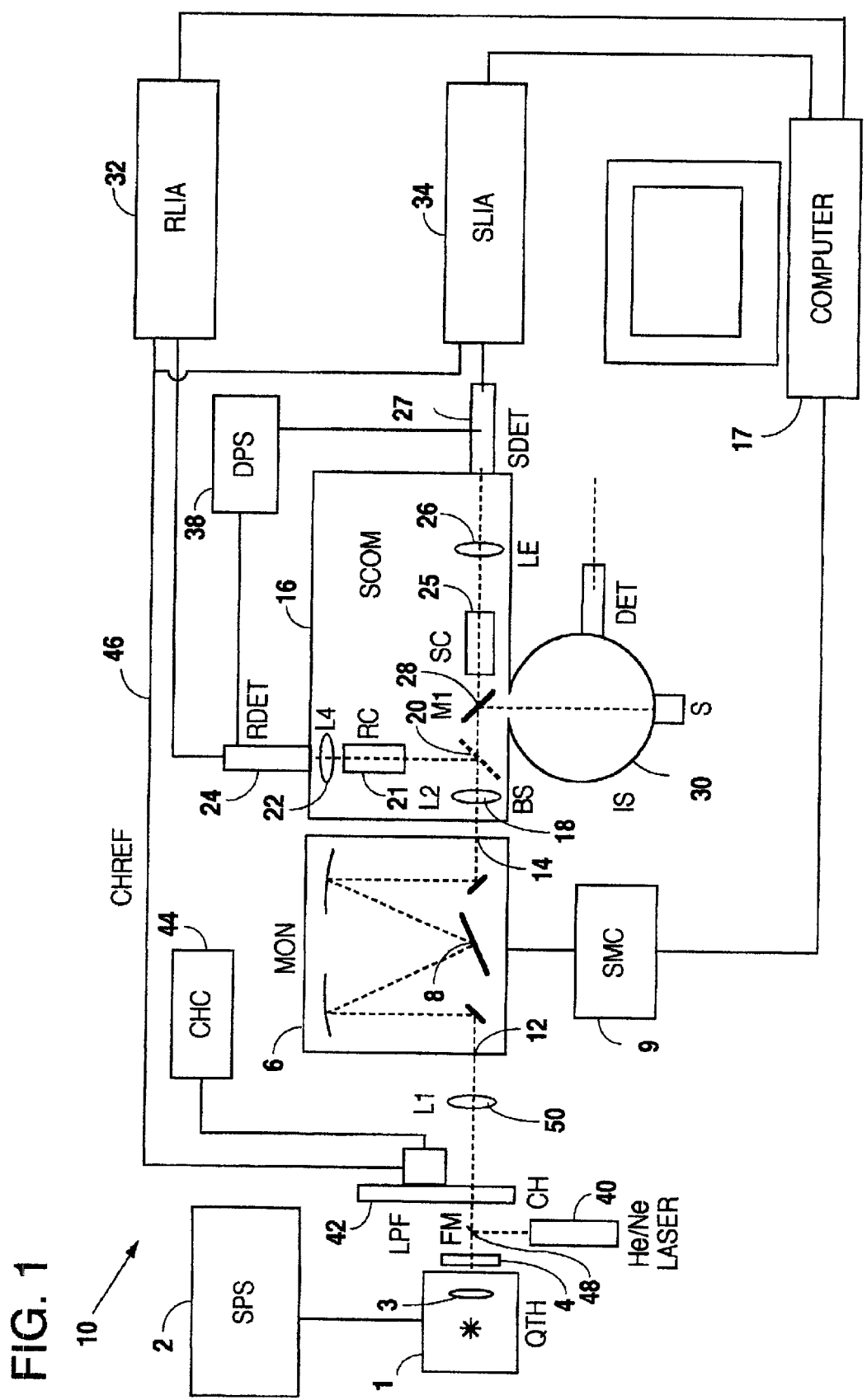
FIG. 1 is a block diagram of the present invention.
Figure 2:
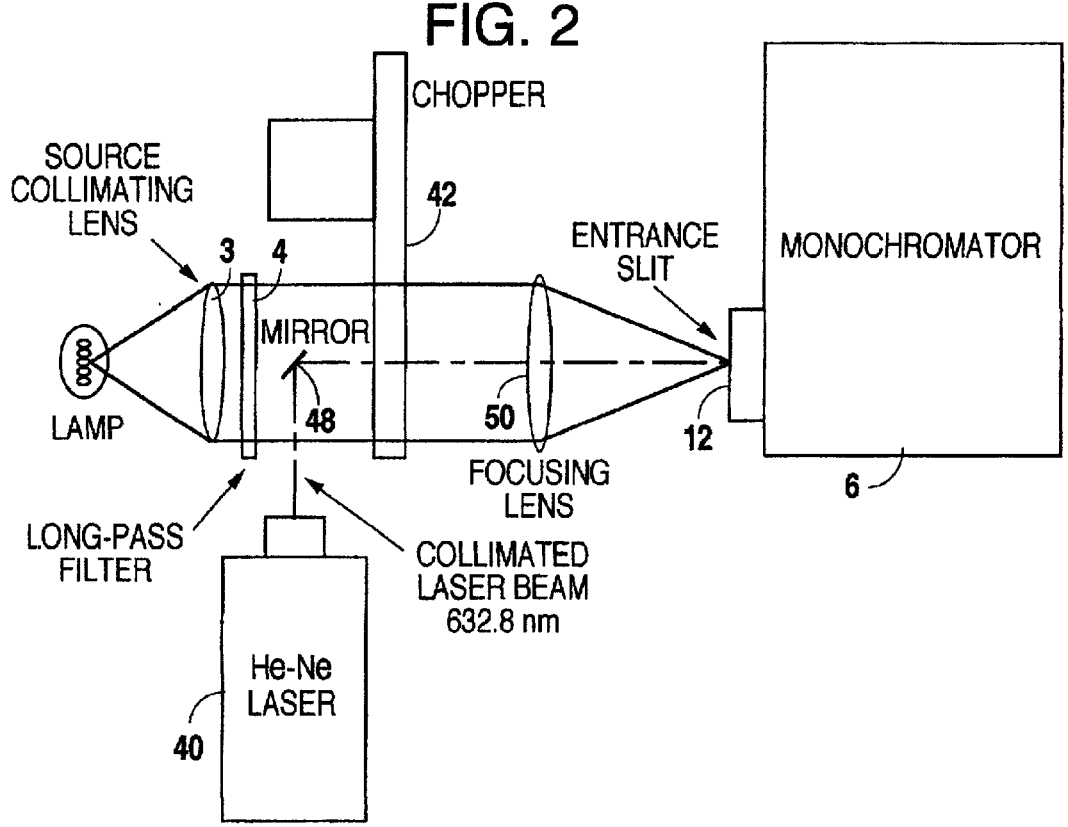
FIG. 2 is an enlarged view diagram of the low power He—Ne laser at a right angle to the source beam of the spectrometer.

The present invention relates to a novel dispersive NIR spectrometer that automatically calibrates the wavelength scale of the instrument without the need for external wavelength calibration materials.[13] This NIR spectrometer with automatic calibration as disclosed herein was developed by the inventor in the laboratory from commercially available component parts in novel combination. The spectrometer is in part based on a spectrometer that has been described previously.[14] The general layout of a spectrometer 10 is seen in FIGS. 1 and 2. First, a 100-W quartz tungsten halogen (QTH) lamp 1 serves as the source beam for the spectrometer 10. The regulated constant-current power supply associated with the source permits source current to to be varied to study its influence in different experiments. It is attached to a source power supply 2. The source beam is focused through a source collimating lens 3. A long-pass cut-on filter 4 with a cut-on wavelength of 1160 nm is attached to the output of the QTH lamp 1 and serves to remove short wavelength radiation from entering the dispersive spectrometer, which otherwise would result in excessively high stray light levels in the instrument. If allowed to remain in the beam, this unwanted shortwave radiation would show up as stray light.[15] A 0.25-m Czerny-Turner monochromator 6, equipped with a 300 line mm$^{-1}$ diffraction grating 8 blazed for 1000 nm, is used as the wavelength dispersive device of the spectrometer 10. With the grating used, the monochromator had a wavelength range between 800–4800 nm and a reciprocal linear dispersion of 12.4 nm mm$^{-1}$ in the first order. The monochromator 6 is attached to a stepping motor control 9, which is in turn connected to a computer 17. The monochromator 6 is fitted with a variable entrance 12 and an exit slit 14.

Figure 4A:
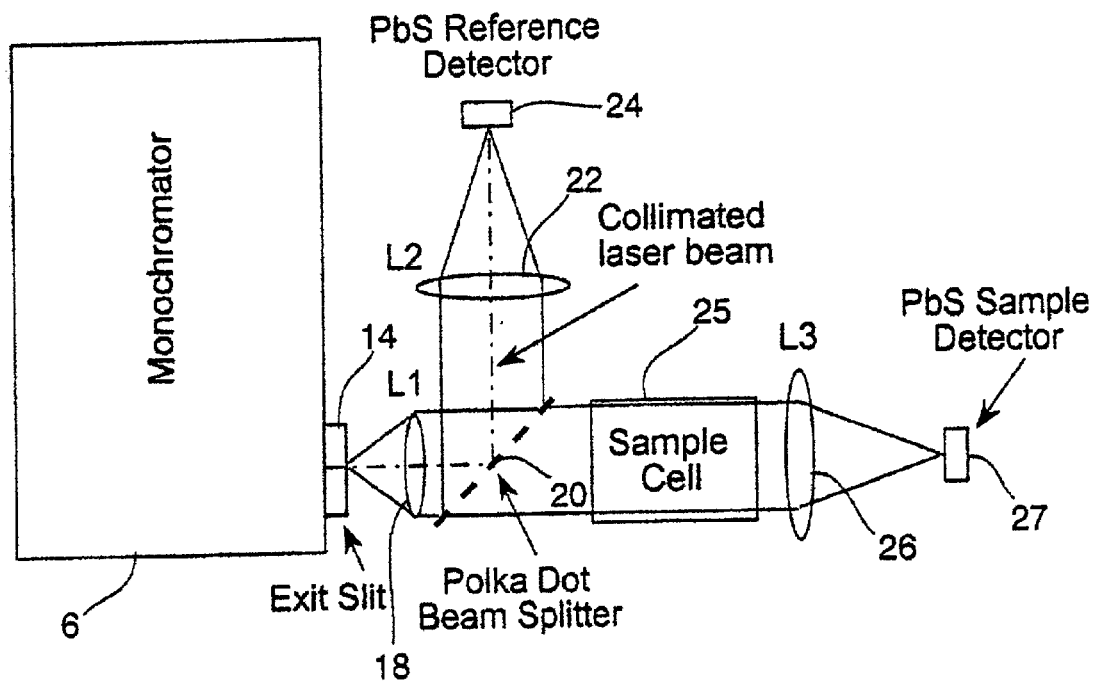
FIG. 4A is a diagram showing a sample compartment.

A specially constructed sample compartment 16, FIGS. 1 and 4A, provides means for double beam operation of the spectrometer. In FIG. 1, radiation emerging from the exit slit 14 of the monochromator 6 is collinated with a lens 18 before being split into two beams by a "polka-dot" beam splitter 20. One beam passes through a reference cell holder 21 and is focused by a lens 22 onto a reference lead sulfide detector or PbS reference detector 24 and the other is passed through a sample 25 before being focused by a lens 26 to strike a sample PbS detector 27. A folding mirror 28 is used only when an integrating sphere 30 is being used. Signals from the respective PbS detectors 24, 27 are demodulated by two lock-in amplifiers 32, 34 before being sent to the data acquisition (DAQ) board of the computer 17. The lock-in amplifiers 32, 34 are referenced to the modulation frequency provided by the rotary chopper 42. Both PbS detectors 24, 27 are connected to a power supply 38.

Figure 3:
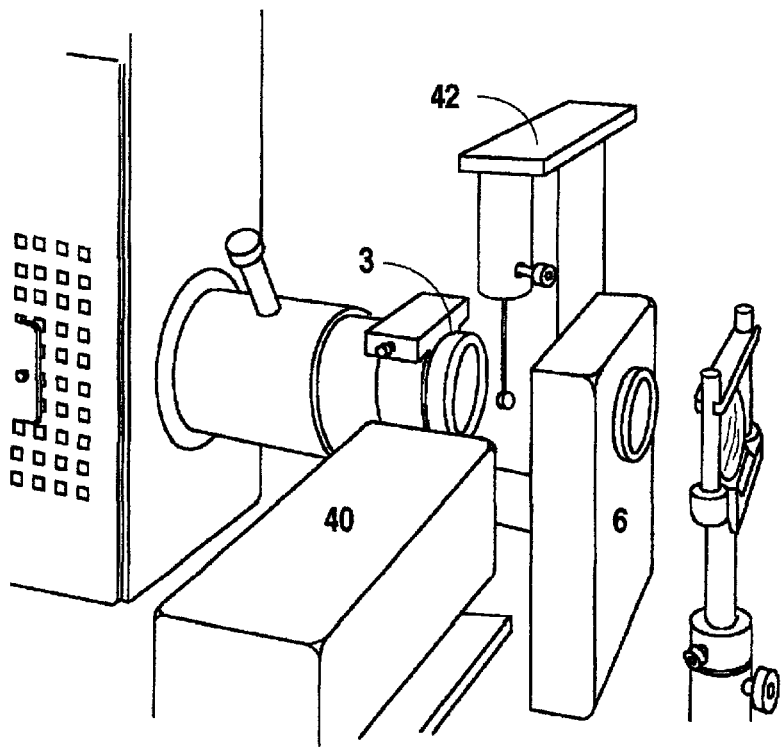
FIG. 3 is a side view of the NIR spectrometer which shows a low power He—Ne laser at right angles to the source beam of the spectrometer.

A preferred embodiment of the present invention is also shown in FIGS. 1, 2, and 3. FIG. 1 shows the modifications that were made to the spectrometer 10 to permit automatic laser wavelength calibration. A 0.5-mW He—Ne laser 40 (Model 79251, Oriel Corp., Stratford, Conn. was used in the laboratory) oriented orthogonally to the QTH lamp beam, was positioned between the QTH lamp 1 and the rotary chopper 42. The rotary chopper 42 is controlled by a chopper controller 44. The rotary chopper 42 reference signal 46 flows from the rotary chopper 42 to the amplifiers 32 and 34. The He—Ne laser 40 produces a single TEM$_{00}$ mode at 632.8 nm and has a nominal beam diameter (1/e$^2$) of 0.48 mm. This is a very narrow collimated beam of light. Radiation from the laser 40 is reflected by 90° with a small folding mirror 48 so that the reflected laser beam is co-linear with the optical path of QTH lamp 1. Because the laser beam is so narrow, the small folding mirror 48 is positioned to redirect the beam without blocking the source beam from the QTH lamp 1 of the spectrometer 10, FIGS. 1, 2, and 3. If a non-laser light source were substituted for the laser 40, it would emit a non-collimated beam that would expand with distance from the source. This would require a larger folding mirror and source radiance would decrease with the square of the distance from the source. Radiation from both the QTH lamp 1 and the laser 40 is then modulated by the rotary chopper 42 before being focused with a lens 50 onto the entrance slit 12 of the monochromator 6.

FIG. 4A shows a schematic diagram of the sample compartment 16 with the polka-dot beam splitter 20 (Model 38106, Oriel). This polka-dot beam splitter 20 (shown in FIGS. 4B and 5) consists of a UV-grade fused silica substrate on which is deposited a pattern of reflective aluminum dots 52, 2.5 mm in diameter, separated by a 3.2 mm center-to-center distance. Since the laser light emerging from the monochromator 6 is still collimated, the polka-dot beam splitter 20 is positioned so that the laser beam emerging from the exit slit 14 of the monochromator 6 hits the polka-dot beam splitter 20 exactly on one of the reflective aluminum dots 52. In this way, radiation from the laser 40 is almost entirely reflected towards the PbS reference detector 24. This would not be possible if a non-laser calibration source were used. PbS detectors 24 and 27 are routinely used for NIR spectroscopy, however their response extends down to 632.8 nm, making them suitable for detecting the laser calibration source while simultaneously detecting the NIR radiation from the QTH lamp 1 of the spectrometer 10.

Principle of Operation

The basic concept behind the laser wavelength calibration system described here is to use a 0.5-mW He—Ne laser 40, FIGS. 1, 2, and 3 to provide known wavelength markers that are recorded simultaneously on the spectrum along with the spectrum of the analyte. These sharp spikes in the spectrum occur at accurately known wavelengths in the spectrum and serve as internal reference points in the spectrum against which the wavelengths of other spectral features may be determined.

The success of the laser wavelength calibration system derives from a combination of factors. First, radiation from a laser 40 is used to provide a small-diameter, highly collimated beam of radiation at an accurately known wavelength, for example, 632.8 nm. Radiation from a He—Ne laser 40 is reflected orthogonally by a small folding mirror 48 so that the laser radiation is co-linear with the beam from the primary QTH lamp 1. The small folding mirror 48 is small (~3 mm diameter) so that it blocks only a tiny fraction of the primary source beam from the QTH lamp 1. Both beams are modulated simultaneously by the rotary chopper 42 and enter the monochromator 6 equipped with the diffraction grating 8.

According to the normal diffraction grating equation 1, $m\lambda=d(\sin i \pm \sin \theta)$, where m is the diffraction order, $\lambda$, is the wavelength, d is the grating constant, i is the angle of incidence, and, $\theta$, is the angle of diffraction. According to Eqn. 1, for a given diffraction grating with fixed i and $\theta$, $m_1\lambda_1=m_2\lambda_2$. This means that 632.8 nm radiation in the second order will appear at the same position as 1266 nm radiation in the first order. Table I gives the apparent positions of 632.8 nm radiation for spectral orders out to six.

TABLE I

Apparent location of 632.8 nm He—Ne laser radiation in first order spectrum.

| Spectral order (m) | Apparent wavelength in first order (nm) |
|---|---|
| 1 | 632.8 |
| 2 | 1266 |
| 3 | 1898 |
| 4 | 2531 |
| 5 | 3164 |
| 6 | 3797 |

It is clear from Table I that the apparent locations of the 632.8 nm laser line are integral multiples of 632.8 and are, therefore, spread uniformly throughout the spectrum at m(632.8) nm, where m is the diffraction order in Eqn. 1. Because the optics of diffraction gratings are well known, the positions of the various spikes can be predicted with great accuracy.

Figure 7:
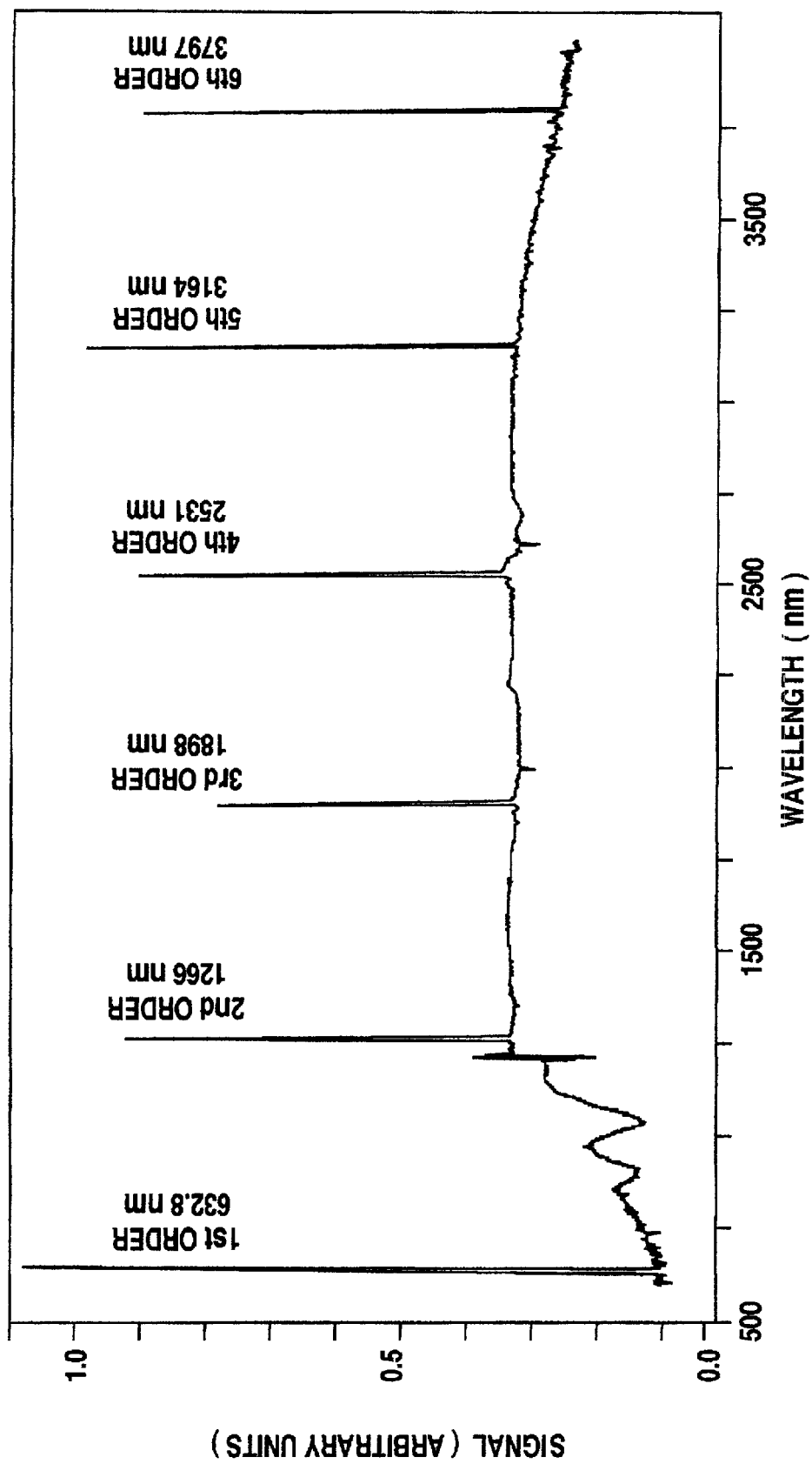
FIG. 7 is a graph showing the apparent locations of the 632.8 nm laser line that appears in different diffraction orders.
Figure 9:
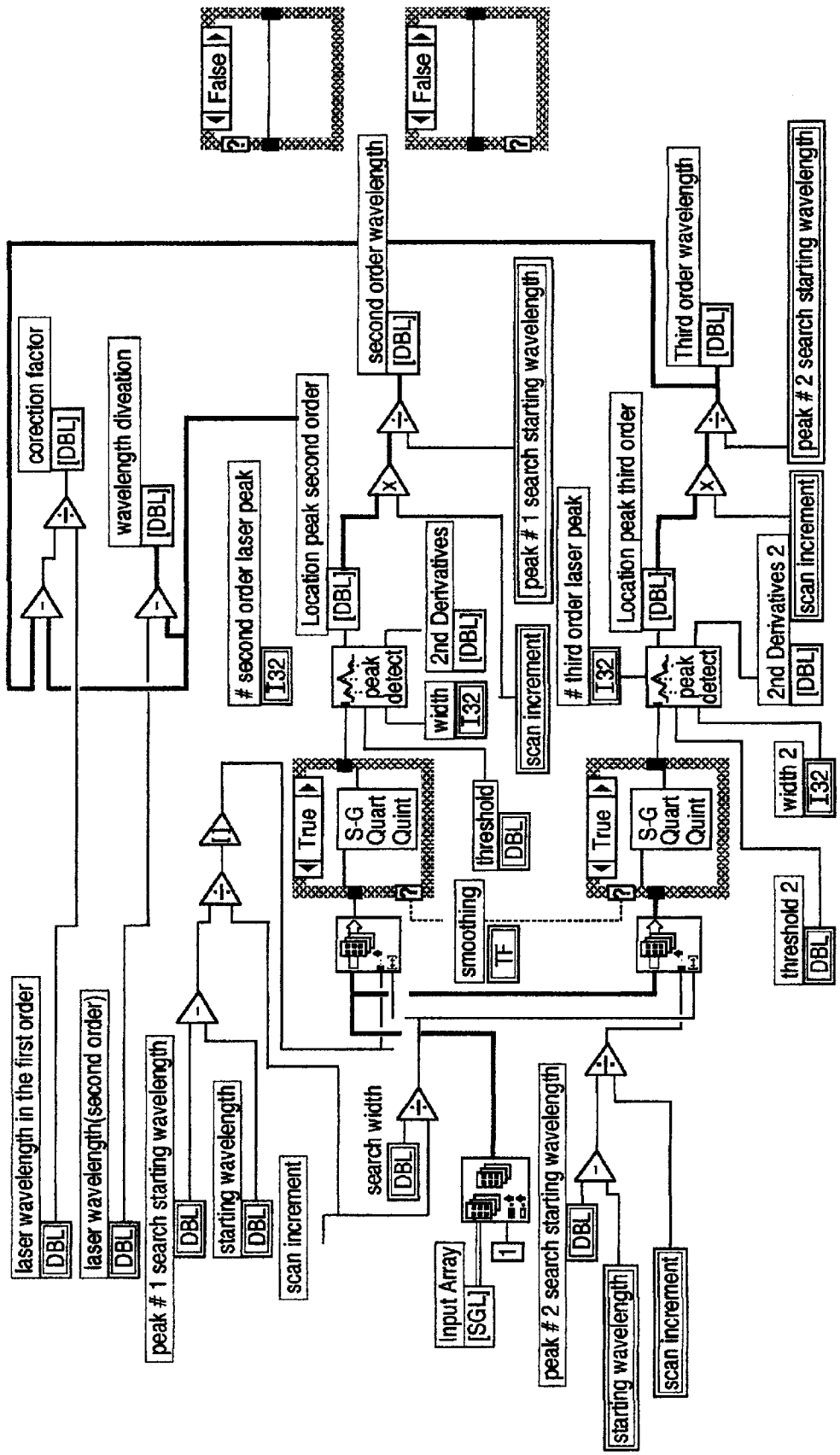
FIG. 9 is a schematic diagram of the LabVIEW program that carries out the mathematical correction of the spectrum.

FIG. 7 shows the sharp spectral features produced by the 632.8 nm He—Ne laser out to 3797 nm (the sixth order!). To produce the spikes shown in FIG. 7, two conditions are required. First, the detector used must respond to radiation at 632.8 nm. While most responsivity data for PbS detectors does not extend below 1000 nm, it is clear from FIG. 7 that the PbS detector does respond to long wavelength visible radiation. Second, the characteristics of the beam splitter in the sample compartment are important.

Figure 4B:
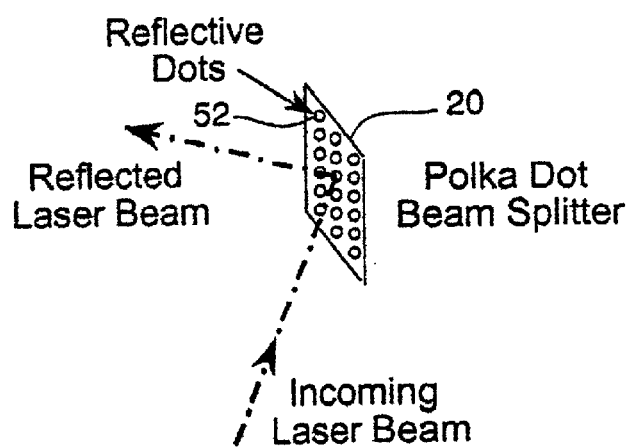
FIG. 4B is a diagram showing a "Polka-dot" beam splitter which directs the majority of the laser beam toward the reference detector.

In laboratory study, the so-called "polka-dot" beam splitter 20, FIGS. 1, 4B and 5, was used that had a pattern of reflective aluminum dots 52 deposited on a fused silica substrate. The reflective aluminum dots 52 were 2.5 mm in diameter and were spaced on 3.2 mm centers. For beams larger than 9.5 mm in diameter, the polka-dot pattern of reflective aluminum dots 52 provides a 50/50 split regardless of the angle of incidence. So, for the larger diameter beam of primary source radiation from the QTH lamp 1, the radiation will be divided approximately equally between the sample and reference beams as desired for double-beam operation. In contrast, by careful placement of the beam splitter 20, radiation from the collimated laser beam emerging from the monochromator 6 can be made to strike on one of the reflective aluminum dots 52. In this way, the laser radiation can be almost entirely directed toward the PbS reference detector 24.

For first-order wavelengths that coincide with the higher diffraction order positions of the 632.8 nm laser line as given in Table I, the intensity of radiation striking the PbS reference detector 24 will go up (i.e., it will consist of radiation from both the QTH lamp 1 and the laser 40). Since absorbance is defined as log ($I_{reference}/I_{sample}$), an increase in $I_{reference}$ will produce an apparent increase in the absorbance at the wavelengths given in Table I. This will result in absorbance spikes at positions given by m(632.8 nm) in the spectrum, where m is an integer.

Table II lists some absorption bands of chloroform recorded with the modified NIR spectrometer that incorporates the He—Ne wavelength marker system and gives the wavelength reproducibility of the prototype instrument.

TABLE II

Wavelength Reproducibility with Laser Spectrometer (nm) Chloroform Bands

| $3v_1$ | $2v_1 + v_4$ | $2v_1$ | $v_1 + 2v_4$ |
|---|---|---|---|
| 1152.04 | 1411.34 | 1692.25 | 1860.19 |
| 1150.12 | 1410.03 | 1691.34 | 1859.92 |
| 1150.71 | 1410.34 | 1691.31 | 1859.79 |
| 1152.14 | 1411.80 | 1692.97 | 1860.95 |
| 1152.03 | 1411.36 | 1692.55 | 1860.73 |
| 1151.41 ± 0.93 | 1410.97 ± 0.75 | 1692.08 ± 0.74 | 1860.32 ± 0.51 |

Figure 10:
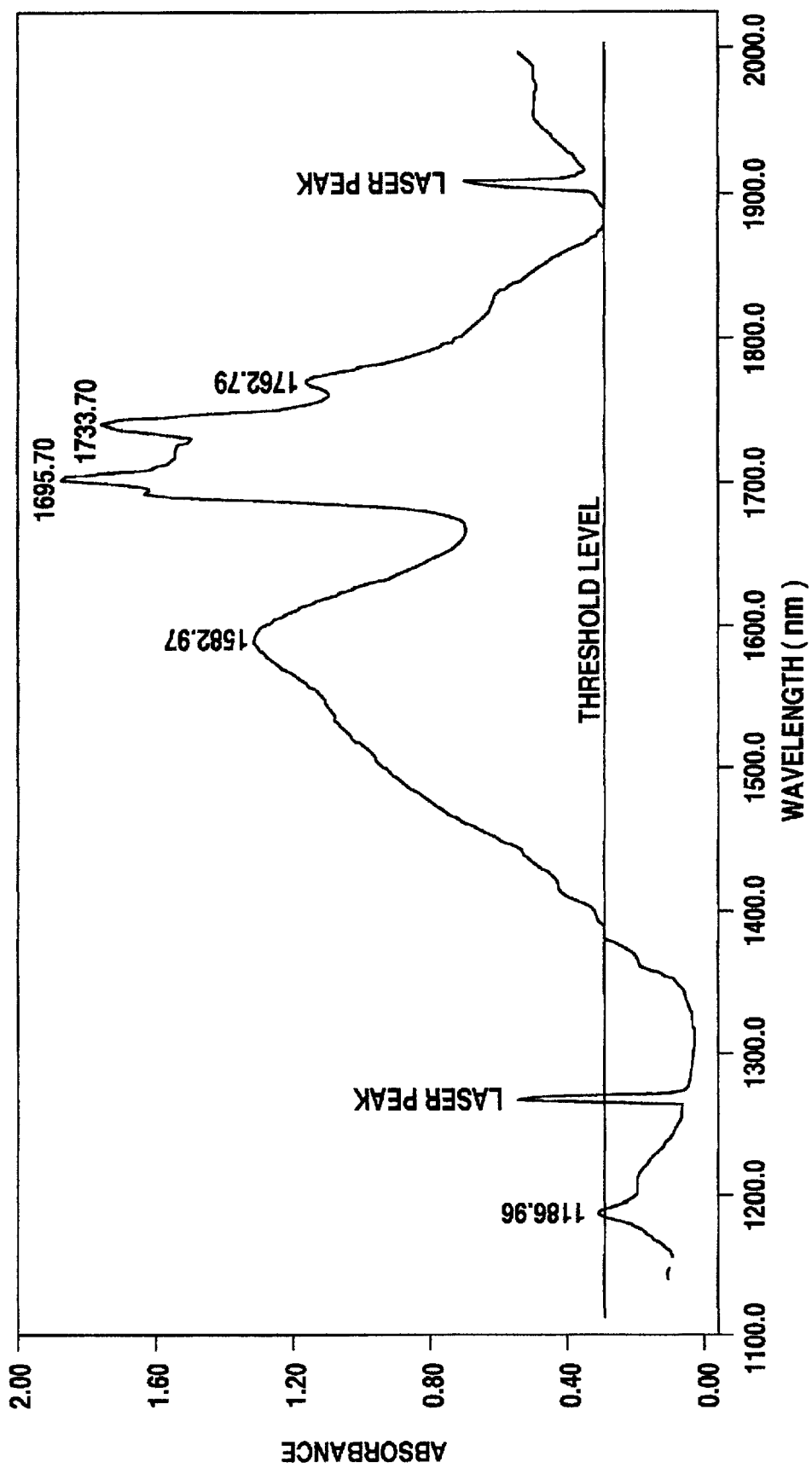
FIG. 10 is a graph showing an NIR spectrum of ethanol with the second and third order laser peaks superimposed.

FIG. 10 shows an NIR spectrum of ethanol with the second and third order laser peaks superimposed. Special software routines developed in the G-programming language, LabVIEW, permit the automatic wavelength calibration of any spectrum taken with the instrument.[13] These software routines are shown in FIGS. 8.1, 8.2 and 9. Software written in LabVIEW detects the peaks produce by the wavelength calibration laser. In normal use, two peaks are used (1265.5 nm and 1898.4 nm). The software performs two basic tasks: a) It shifts the spectrum left or right as needed so that the laser peak at 1265.6 nm falls at the correct position. It then uses the separation between the 1265.6 nm peak and the 1898.4 nm peak to correct the dispersion of the instrument. Spectra are plotted with a graphical-user interface created with LabVIEW™. Peak positions in the dispersive spectra are determined with a peak-locating routine that is part of the LabVIEW graphing software.™ Because of the many advantages of LabVIEW for instrument control and data acquisition, its use in different areas of instrumental development is widespread.[17-21] LabVIEW uses the G-programming language to create graphical computer interface (data flow) programs known as virtual instruments (VI's). Virtual instruments are modular and hierarchical so that they are not only easy to debug, but they can also act as "stand alone" units or sub-VI's. Different sub-VI's can be "pooled" together to create multi-faceted application programs that are flexible enough to be easily modified to meet the needs of different experiments. VI's are divided into three parts[22]. 1) The front panel is the interactive part of the program and mimics the actual instrument. 2) The block diagram contains the source code written in the G-programming language. 3) The icon represents the VI in the block diagram of another VI. The icon has connectors that allow the flow of data into and out of the VI. FIG. 6 shows the mathematical basis for the software.

Unlike the instant invention, calibration of the wavelength scale of a FT-NIR spectrometer is often necessary due to small, inevitable misalignments of the He—Ne reference laser which introduce small wavelength shifts in the interferogram that compromise the wave number accuracy of the FT-NIR spectrometer[23]. Tests with the invention assembled in the laboratory have revealed that the laser wavelength calibration system performs comparably to a FT-NIR spectrometer when used to determine the absorption wavelengths for trichloromethane. Table III compares the wavelength accuracy of the laser spectrometer with a commercial Fourier transform NIR spectrometer.

TABLE III

Accuracy of Laser Spectrometer compared with FTNIR

| FTNIR (nm) | dispersive (nm)[a] | Deviation (nm) |
|---|---|---|
| 1151.44[a] | 1151.68 | +0.24 |
| 1410.04[a] | 1411.04 | +1.00 |
| 1692.82[a] | 1692.10 | −0.72 |
| 1860.02[b] | 1860.29 | +0.27 |
|  | Ave. Absolute Dev. | 0.53 |

[a]Average of two sets of five measurements
[b]Average of one set of five measurements While the invention has been described with a certain degree of particularity, it is manifest that many changes may be made in the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

Design and Evaluation of a Near-Infrared Dispersive Spectrometer that Uses a He—Ne Laser for Automatic Internal Wavelength Calibration A diffraction-grating near-infrared spectrometer that uses a He—Ne laser for automatic internal wavelength calibration is described. The instrument uses the known location of the higher diffraction orders of the 632.8 nm laser line to perform wavelength calibration in the near-infrared region with a program written in LabVIEW. The wavelength accuracy of the dispersive spectrometer was compared with that of a Fourier-transform near-infrared spectrometer whose wavelength scale was validated by calibration with the known spectrum of ethyne. The average absolute wavelength deviation between the two spectrometers for four isolated bands of trichloromethane was found to be +0.12 nm. The average values of the wavelengths of four isolated bands of trichloromethane obtained with the two spectrometers used in this study were determined to be: 1151.62±0.28 nm ($3v_1$), 1410.74±0.52 nm ($2v_1+V_4$), 1692.38±0.49 nm ($2v_1$), and 1860.20±0.16 nm ($v_1+2v_4$) Index Headings: Near Infrared Spectroscopy; Wavelength Calibration; Spectrometer calibration; NIR spectrum of trichloromethane.

Introduction

Near-infrared (NIR) spectroscopy has been shown to be a powerful analytical tool for the analysis of agricultural products, food products, petroleum products, and pharmaceuticals[1,2]. In general, when NIR spectroscopy is combined with multivariate calibration procedures, the analytical methodology that results is rapid, accurate, and requires virtually no sample preparation.

In conventional NIR spectroscopy, a multivariate statistical model is developed that attempts to correlate subtle changes in the NIR spectrum with known compositional changes determined by standard analytical technology. Once a robust model has been developed, NIR spectroscopic measurements can be substituted for the more time consuming, labor-intensive conventional analytical measurements. To be completely useful, however, a model developed on one spectrometer in the laboratory should be capable of being used on different spectrometers without having to go through the model development all over again with the new instrument. To transfer a model from one spectrometer to another successfully, both instruments must ideally be identical.

In reality, different spectrometers are subtly different. One factor that can have a significant impact on calibration transfer is wavelength accuracy, particularly with dispersive spectrometers. If the wavelength scales of different spectrometers are miscalibrated (as they inevitably are), problems with calibration transfer may occur. One way to avoid this problem is to use a wavelength standard to validate the wavelength scale of the spectrometer. Recently, Busch and co-workers have proposed the use of trichloromethane as a substance with sharp, isolated absorption bands that are suitable for wavelength calibration of spectrometers in the NIR region[3]. This paper describes an instrumental approach that automatically calibrates the wavelength scale of a dispersive NIR spectrometer without the need for external wavelength calibration materials.

Experimental

FIG. 1 shows the general features of the NIR spectrometer used in this study. The spectrometer, which was assembled from commercially available component parts and has been described in detail previously[4], can be used in both the transmission and reflectance modes (only the transmission mode is shown). A 100-W quartz tungsten halogen (QTH) lamp (Model 66181, Oriel, Stratford, Conn.) served as the source for the spectrometer. A long-pass cut-on filter with a cut-on wavelength of 1160 nm (Spectrogon, Parsippany, N.J.) was attached to the output of the QTH lamp and served to remove short wavelength radiation from entering the dispersive spectrometer, which otherwise would have resulted in excessively high stray light levels in the instrument. A 0.25-m Czerny-Turner monochromator (Model 77200, Oriel), equipped with a 300 line mm$^{-1}$ diffraction grating blazed for 1000 nm, was used as the wavelength dispersion device of the spectrometer. The monochromator was fitted with variable entrance and exit slits.

To permit laser wavelength calibration, a 0.5-mW He—Ne laser (Model 79251, Oriel Corp., Stratford, Conn.), oriented orthogonally to the QTH lamp beam, was positioned between the QTH lamp and the chopper as shown in FIG. 1. The laser produced a single TEM$_{00}$ mode at 632.8 nm and had a nominal beam diameter ($1/e^2$) of 0.48 mm. Radiation from the laser was reflected by 90° with a small folding mirror so that the reflected laser beam was co-linear with the optical path of QTH lamp. Radiation from both the QTH lamp and the laser was then modulated by the rotary chopper before being focused with a lens onto the entrance slit of the monochromator.

A specially constructed sample compartment provided means for double-beam operation of the spectrometer. Radiation emerging from the exit slit of the monochromator was split into two beams by a "polka-dot" beam splitter (Model 38106, Oriel). This beam splitter consisted of a UV-grade fused silica substrate on which was deposited a pattern of reflective aluminum dots, 2.5 mm in diameter, separated by a 3.2 mm center-to-center distance. The beam splitter was positioned so that the laser beam emerging from the exit slit of the monochromator hit the beam splitter exactly on one of the reflective aluminum dots. In this way, radiation from the laser was almost entirely reflected towards the reference PbS detector. The other beam was focused on the sample PbS detector. Signals from the respective PbS detectors were demodulated by two lock-in amplifiers (Model 3962A, Ithaco, Ithaca, N.Y.) before being sent to the data acquisition (DAQ) board of the computer.

Overall spectrometer control was accomplished with a program written in LabVIEW™ version 5.1 (National Instruments, Austin, Tex.).

Results and Discussion

Principle of Operation. The basic concept behind the laser wavelength calibration system described here is to use a 0.5-mW He—Ne laser to provide known wavelength markers that are recorded simultaneously on the spectrum along with the spectrum of the analyte. These sharp spikes in the spectrum occur at accurately known wavelengths in the spectrum and serve as internal reference points in the spectrum against which the wavelengths of other spectral features may be determined.

The success of the laser wavelength calibration system derives from a combination of factors. First, radiation from a laser is used to provide a small-diameter, highly collimated beam of radiation at an accurately known wavelength (632.8 nm). Radiation from a He—Ne laser is reflected orthogonally by a small mirror so that the laser radiation is co-linear with the beam from the primary QTH lamp. The folding mirror is small (~3 mm diameter) so that it blocks only a tiny fraction of the primary source beam from the QTH lamp.

Both beams are modulated simultaneously by the rotary chopper and enter the monochromator equipped with the diffraction grating. According to the normal diffraction grating equation[5], $$m\lambda = d(\sin i \pm \sin \theta) \quad (1)$$

where m is the diffraction order, $\lambda$ is the wavelength, d is the grating constant, i is the angle of incidence, and $\theta$ is the angle of diffraction. According to Eqn. 1, for a given diffraction grating with fixed i and $\theta$, $m_1\lambda_1 = m_2\lambda_2$.

It is clear from Eqn. 1 that the apparent locations of the 632.8 nm laser line in higher orders should be integral multiples of 632.8 and should, therefore, be spread uniformly throughout the spectrum at m(632.8) nm, where m is the diffraction order in Eqn. 1. Because the optics of diffraction gratings are well known, the positions of the various spikes can be predicted with great accuracy.

Figure 11:
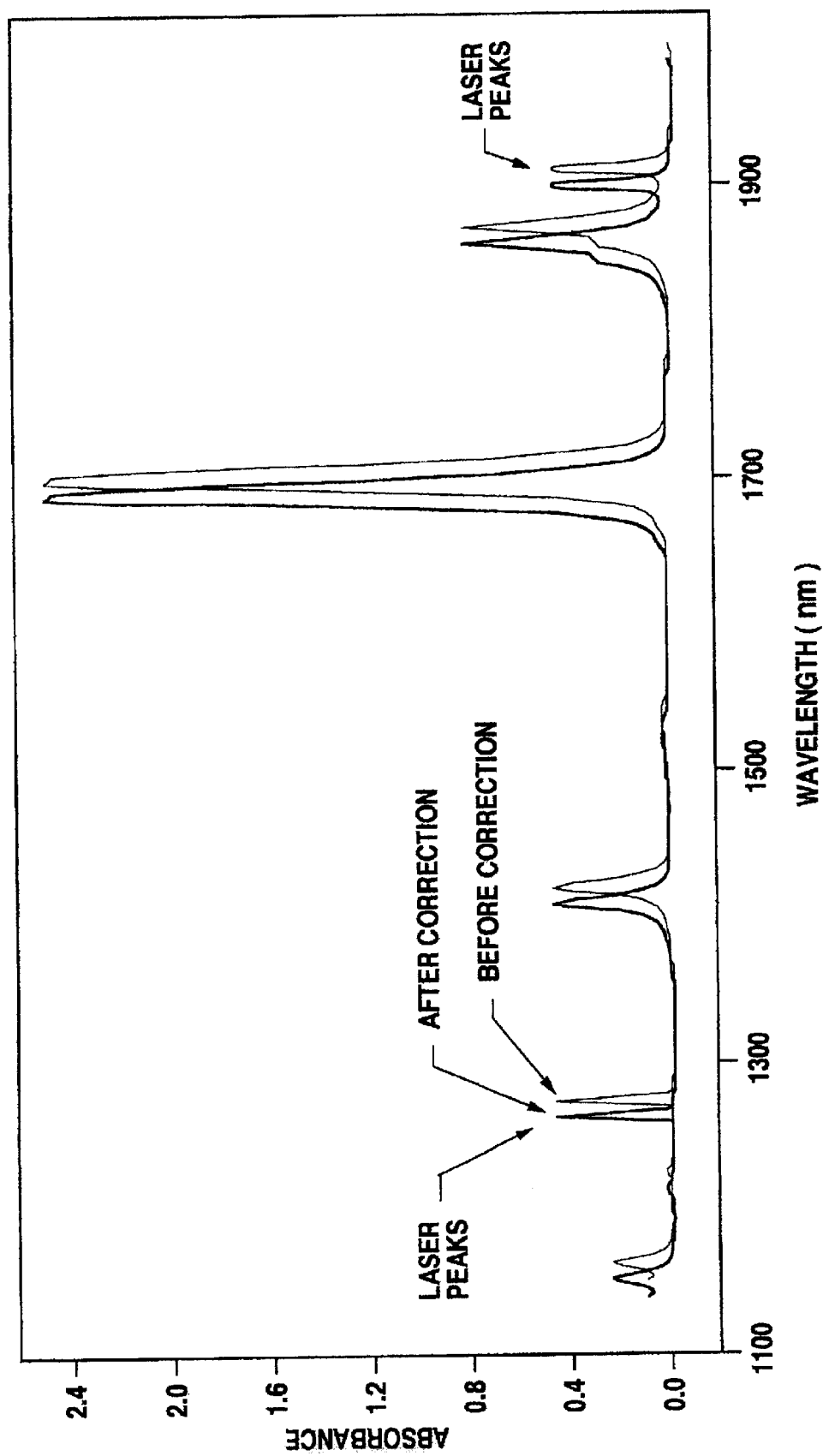
FIG. 11 is a graph showing the spectrum trichloromethane before and after laser wave length correction.

FIG. 11 shows the spectrum of He—Ne laser from 500 to 4000 nm showing the location of the higher-order diffraction peaks. The sharp spectral features produced by the 632.8 nm He—Ne laser out to 3797 nm (the sixth order!) are shown. To produce the spikes shown in FIG. 11, two conditions are required. First, the detector used must respond to radiation at 632.8 nm. While most responsivity data for PbS detectors does not extend below 1000 nm[6], it is clear from previous work[7] and from FIG. 11 that the PbS detector does respond to long wavelength visible radiation.

Second, the characteristics of the beam splitter in the sample compartment are important. In this study, a so-called "polka-dot" beam splitter was used that had a pattern of reflective aluminum dots deposited on a fused silica substrate. The reflective aluminum dots were 2.5 mm in diameter and were spaced on 3.2 mm centers. For beams larger than 9.5 mm in diameter, the polka-dot pattern of reflective aluminum dots provides a 50/50 split regardless of the angle of incidence. So, for the larger diameter beam of primary source radiation from the QTH lamp, the radiation will be divided approximately equally between the sample and reference beams as desired for double-beam operation. In contrast, by careful placement of the beam splitter, radiation from the collimated laser beam emerging from the monochromator can be made to strike on one of the reflective aluminum dots. In this way, the laser radiation can be almost entirely directed toward the reference PbS detector.

For first-order wavelengths in the NIR region that coincide with the higher diffraction order positions of the 632.8 nm laser line, the intensity of radiation striking the reference detector will go up (i.e., it will consist of radiation from both the QTH lamp and the laser). Since for this spectrometer, absorbance is defined as log $(I_{reference}/I_{sample})$, an increase in $I_{reference}$ will produce an apparent increase in the absorbance at the wavelengths that correspond to higher diffraction orders of 632.8 nm radiation. This will result in absorbance spikes at positions given by m(632.8 nm) in the spectrum, where m is an integer.

Software Control

Overall spectrometer control was accomplished with a program written in LabVIEW version 5.1. For this application, a menu is used to call any one of several virtual instruments (VIs) that allow the user to operate the spectrometer, as well as plot and manipulate data. The complete-plotter VI calls data files, plots spectra, and saves the spectral data with any modifications to another file. Other options include taking derivatives, data smoothing, listing peak locations above an adjustable threshold, and utilization of the laser-calibration option. When the laser-calibration option is selected, the VI corrects the spectrum using parameters calculated in a sub-VI. This sub-VI uses a peak-finding routine available in LabVIEW to locate the laser peaks and determine the parameters used in the complete-plotter VI to calibrate the spectrum.

Equation 2 gives the algorithm that was used for wavelength correction, $$\lambda_{corrected} = (\lambda_{measured} + \Delta) + \beta(\lambda_{measured} - \lambda_{2nd\ order}) \quad (2)$$

where $\lambda_{corrected}$ and $\lambda_{measured}$ are the corrected and measured values of the wavelength in nanometers, respectively, $\Delta$ is $1265.6 - \lambda_{2nd\ order}$, $\beta$ is $1-\alpha$, $\alpha$ is $(\lambda_{3rd\ order} - \lambda_{2nd\ order})/632.8$, and $\lambda_{2nd\ order}$ and $\lambda_{3rd\ order}$ are the measured values of the second and third order absorbance peaks produced by the laser. The first term in Eqn. 2 shifts the spectrum left or right on the wavelength scale while the second term corrects the dispersion.

Instrument Performance. FIG. 10 shows the NIR spectrum of ethanol over the wavelength range from 1100 to 2000 nm obtained with the instrument. The spectrum clearly shows the $2^{nd}$ and $3^{rd}$ order absorbance peaks produced by the laser. The threshold level has been set to identify the corrected wavelengths of the more prominent peaks in the spectrum.

It should also be noted that this laser calibration system can be used in two modes of operation. In one mode, the laser peaks are present in the sample spectrum as shown in FIG. 10 and the calibration is done after the spectrum has been taken. Alternatively, the system can also be used by taking a spectrum of the laser radiation without a sample present and plotting the corrected wavelengths against the uncorrected ones. A correlation equation can then be determined that can be incorporated into the scanning VI. This calibration equation can then be periodically verified as needed.

To validate the performance of the laser spectrometer, the spectrum of trichloromethane was studied with the laser-corrected spectrometer and a Fourier-transform NIR (FTNIR) spectrometer (Cygnus-25, Mattson Instruments, Madison, Wis.). The wavenumber scale of the FTNIR was calibrated as described previously[3].

Table IV shows the wavelength reproducibility obtained from 5 spectra with four trichloromethane bands when laser wavelength calibration is employed. Use of laser wavelength calibration improves the wavelength reproducibility of the spectrometer and reduces the uncertainty in the measured wavelength values to less than 1 nm (average value 0.73 nm).

Table V compares the wavelengths for four bands in the trichloromethane spectrum obtained with the FTNIR spectrometer and the dispersive spectrometer with laser wavelength calibration. The agreement between the two spectrometers is quite good with an average absolute deviation for the four bands of +0.12 nm.

In previous work on the use of trichloromethane as an NIR wavelength standard, a calibrated FTNIR spectrometer was used to determine the wavelength of four bands in the trichloromethane NIR spectrum[3]. In this study, the wavelengths of these same bands were re-measured with a calibrated FTNIR spectrometer and compared with those obtained with the laser-corrected spectrometer. Table VI summarizes the wavelength values obtained to date for the four trichloromethane bands that have been proposed as wavelength standards for NIR spectroscopy. The results obtained in this study with the FTNIR spectrometer and the laser-corrected dispersive spectrometer are in substantial agreement. Table VI also reports the average values for the wavelengths of the four bands obtained with the two spectrometers used in this study.

CONCLUSIONS

Incorporation of a He—Ne laser into a dispersive NIR spectrometer that employs a diffraction grating dispersion system permits wavelength calibration of the instrument based on the known locations of the higher diffraction order positions of the 632.8 nm laser line. Over the spectral range from 1100 to 2000 nm, both the second and third order positions of the 632.8 nm laser line are observed and can be used as markers for wavelength calibration. Agreement between the band positions for chloroform obtained with an FTNIR spectrometer and the dispersive spectrometer with laser wavelength calibration is quite good. The factors that contribute to the proper functioning of the wavelength correction system are: 1) the He—Ne laser emits a sharp, isolated line of known wavelength (632.8 nm); 2) the PbS detector responds to the radiation emitted by the He—Ne laser; 3) the diffraction grating produces multiple orders (out to six) so that the 632.8 nm line appears at known multiples of 632.8 nm in the NIR region; 4) the laser produces a small diameter, collimated beam so that a small mirror can be used to fold the laser radiation into the source beam without obstructing much light from the source beam; 5) a polka dot beam splitter can be arranged so that the laser beam emerging from the monochromator strikes a reflective dot on the beam splitter and is thereby preferentially reflected towards the reference detector; 6) a program written in LabVIEW can be used to perform the wavelength calibration with a simple algorithm.

REFERENCES

The following citations are incorporated by reference herein for details supplementing this application:

1. B. G. Osborne, T. Fearn, and P. H. Hindle, *Practical NIR Spectroscopy with Applications in Food and Beverage Analysis* (Longman Scientific & Technical, Essex, England, 1993).
2. Donald A. Burns and Emil W. Ciurszak, Eds., *Handbook of Near-Infrared Analysis* (Marcel Dekker, New York, 1992)
3. Kenneth W. Busch, Olusola Soyemi, Dennis Rabbe, Karalyn Humphrey, Ben Dundee, and Marianna A. Busch, Appl. Spectrosc. 54, 1321 (1999).
4. Olusola Soyemi, Dennis Rabbe, Ben Dundee, Marianna A. Busch, and Kenneth W. Busch, Spectrosc. 16(4), 24 (2001).
5. Kenneth W. Busch and Marianna A. Busch, *Multielement Detection Systems for Spectrochemical Analysis* (John Wiley and Sons, New York, 1990) p. 91.
6. William L. Wolfe and George J. Zissis, Eds., *The Infrared Handbook* (Office of Naval Research, Department of the Navy, Washington, D.C., 1985) p. 11–70.
7. Kenneth W. Busch, Olusola Soyemi, Dennis Rabbe, and Marianna A. Busch, Appl. Spectrosc. 54, 1759 (2000).

TABLE IV

Wavelength reproducibility obtained with the laser-corrected spectrometer for four trichloromethane bands (nm)[a].

| Trichloromethane Bands | | | |
|---|---|---|---|
| $3\nu_1$ | $2\nu_1 + \nu_4$ | $2\nu_1$ | $\nu_1 + 2\nu_4$ |
| 1152.04 | 1411.34 | 1692.25 | 1860.19 |
| 1150.12 | 1410.03 | 1691.34 | 1859.92 |
| 1150.71 | 1410.34 | 1691.31 | 1859.79 |
| 1152.14 | 1411.80 | 1692.97 | 1860.95 |
| 1152.03 | 1411.36 | 1692.55 | 1860.73 |
| 1151.41 ± 0.93 | 1410.97 ± 0.75 | 1692.08 ± 0.74 | 1860.32 ± 0.51 |

[a]0.3 mm slit width

TABLE V

Comparison of the wavelengths of four trichloromethane bands obtained with a FTNIR spectrometer and the dispersive NIR spectrometer using laser wavelength calibration.

| FTNIR (nm)[a] | Dispersive (nm)[b] | Deviation (nm) |
|---|---|---|
| 1151.53 | 1151.68 | +0.15 |
| 1410.14 | 1411.04 | +0.90 |
| 1692.95 | 1692.10 | −0.85 |
| 1860.02 | 1860.29 | +0.27 |
|  | Ave. Absolute Dev. | +0.12 |

[a]Average of five measurements
[b]Average of two sets of five measurements

TABLE VI

Summary of wavelength values obtained for four trichloromethane bands proposed as wavelength standards for NIR spectroscopy (nm).

| Assignment | $3\nu_1$ | $2\nu_1 + \nu_4$ | $2\nu_1$ | $\nu_1 + 2\nu_4$ |
|---|---|---|---|---|
| FTNIR, previous study[a] | 1152.13 ± 0.01 | 1410.21 ± 0.01 | 1691.9 ± 0.7 | 1861.22 ± 0.01 |
| FTNIR, this study[b] | 1151.53 ± 0.08 | 1410.14 ± 0.02 | 1692.95 ± 0.08 | 1860.02 ± 0.27 |

TABLE VI-continued

Summary of wavelength values obtained for four trichloromethane bands proposed as wavelength standards for NIR spectroscopy (nm).

| Assignment | $3v_1$ | $2v_1 + v_4$ | $2v_1$ | $v_1 + 2v_4$ |
|---|---|---|---|---|
| Dispersive (0.3 mm slit), this study[c] | 1151.41 ± 0.93 | 1410.97 ± 0.75 | 1692.08 ± 0.74 | 1860.32 ± 0.51 |
| Dispersive (0.4 mm slit), this study[c] | 1151.94 ± 0.27 | 1411.11 ± 0.09 | 1692.11 ± 0.14 | 1860.25 ± 0.25 |
| Average[d] | 1151.62 ± 0.28 | 1410.74 ± 0.52 | 1692.38 ± 0.49 | 1860.20 ± 0.16 |

[a]ref. 3
[b]Corrected with ethyne spectrum
[c]Corrected with laser calibration
[d]Values obtained in this study (both FTIR and dispersive)

REFERENCES

The following citations are incorporated by reference herein for details supplementing this application:

1. Donald A. Burns and Emil W. Ciurczak, *Handbook of Near-Infrared Analysis* (Dekker, New York, 1992).
2. H. Martens and T. Naes, *Multivariate Calibration* (Wiley, New York, 1989).
3. T. B. Blank, S. T. Sum, S. D. Brown, and S. L. Monfre, *Anal. Chem.* 68, 2987 (1996).
4. J. J. Workman, P. R. Mobley, B. R. Kowalski, and Ramus Bro, *Appl. Spectrosc. Rev.* 31, 73.
5. J. J. Workman and J. Coates, *Spectroscopy* 8, 36 (1993).
6. Y. Wang, D. J. Veltkamp, and B. R. Kowalski, *Anal. Chem.* 63, 2750 (1991).
7. SRM 1920a: *Near Infrared Reflectance Wavelength Standard* (National Institute of Standards and Technology, Gaitherburg, Md., 1999)
8. SRM 2517: *Wavelength Reference Absorption Cell* (National Institute of Standards and Technology, Gaitherburg, Md., 1999).
9. SRM 2035: *Near Infrared Transmission Wavelength Standard from* $10,300 \; cm^{-1}$ *to* $5130 \; cm^{-1}$ (National Institute of Standards and Technology, Gaitherburg, Md., 1999).
10. Stephen R. Lowry, Jim Hyatt, and William J. McCarthy, *Appl. Spectrosc.* 54, 450 (2000),
11. Kenneth W. Busch, Olusola Soyemi, Dennis Rabbe, Karalyn Humphrey, Ben Dundee, and Marianna A. Busch, *Appl. Spectrosc.*, 54, 1321 (2000).
12. Kenneth W. Busch, Olusola Soyemi, Benn Dundee, Dennis Rabbe, and Marianna A. Busch, *Spectrosc.*, 16(4), 24–33, April, 2001.
13. Marianna Busch, Dennis Rabbe, Karalyn Humphrey, and Kenneth W. Busch, "Design and Evaluation of a Near-Infrared Dispersive Spectrometer that uses a He—Ne Laser for Automatic Internal Wavelength Calibration," 27th Annual Conference of the Federation of Analytical Chemistry and Spectroscopy Societies, Nashville, Tenn., Sept. 25, 2000, Paper No. 108.
14. Soyemi, *Design of Data Acquisition and Analysis Systems in Near-Infrared Spectroscopy: A Virtual Instrument Approach*, Ph.D. Dissertation, Baylor University, January, 2000.
15. Kenneth W. Busch, Olusola Soyemi, Dennis Rabbe, and Marianna A. Busch, *Appl. Spectrosc.*, 54, 1759 (2000.
16. Soyemi, Design of Data Acquisition and Analysis Systems in Near-Infrared Spectroscopy: A Virtual Instrument Approach, Ph.D. Dissertation, Baylor University, January, 2000.
17. Christopher G. Wiggenstein, Kirk H. Schulz, and Joe Scott, *Rev. Sci. Instrum.* 69, 3707 (1998).
18. Michel Koenig, Jean M. Boudenne, P. Legriel, A. Legriel, T. Grandpierre, Dimitri Batani, Simone Bossi, Sonia Nicolella, and René Benattar, *Rev. Sci. Instrum.* 68, 2387 (1997).
19. I. W. Kirkman and P. A. Buksh, *Rev. Sci. Instrum.* 63, 869 (1992).
20. Wieslaw J. Stryewski, *Rev. Sci. Instrum.* 62, 1921 (1991).
21. F. J. S. de Viteri and D. Diamond, *Analytical Proceedings including Analytical Communications*, 31, 229 (1994).
22. L. K. Wells, LabVIEW: Student Edition Users' Guide (Prentice Hall, Upper Saddle River, N.J., 1994).
23. Peter R. Griffiths and James A. de Haseth, *Fourier Transform Infrared Spectrometry*, (Wiley, New York, 1986).

What is claimed is:

1. An improved spectrometer capable of automatic calibration of the wavelength scale of the instrument without the need for external wavelength calibration means, the improved spectrometer comprising:

a source of polychromatic radiation capable of the emission of a source beam of NIR radiation;

a collimating lens for collimating the source beam radiation;

a laser capable of emitting a substantially monochromatic beam of laser light;

a monochromator for receiving a composite beam, the composite beam comprised of said laser light and said source beam radiation, for dispersion of the source radiation into discrete wavelengths;

a reference detector for detecting radiation and emitting a signal proportional thereto;

a sample container containing a sample;

a sample detector for detecting radiation and emitting a signal proportional thereto;

a beam splitter for receiving the composite beam, the beam splitter capable of directing some of the source radiation through the sample container to the sample detector, the beam splitter further capable of directing some of the laser radiation to the reference detector;

a computer for receiving signals from the reference detector and the sample detector; and software in operable engagement with the computer to analyze the signals from the reference detector and the sample detector and to calibrate the sample detector signals with the reference detector signals.

2. The spectrometer of claim 1, wherein the laser is set at right angles to a source beam of the spectrometer and further including a folding mirror to direct the laser light so that it is parallel to the source beam.

3. The spectrometer of claim 1, wherein the laser is a He—Ne laser.

4. The spectrometer of claim 1, further comprising a folding mirror to redirect the He—Ne laser beam so that it is parallel to a source beam.

5. The spectrometer of claim 1, wherein the laser at right angles to a source beam of the spectrometer where the He—Ne laser emits a collimated laser beam with a wavelength of 632.8 nm.

6. The spectrometer of claim 1, further comprising a mirror to redirect the laser beam so that it is parallel to the source beam.

7. The spectrometer of claim 1, wherein the beam splitter is a "Polka-dot" beam splitter.

8. The spectrometer of claim 1, wherein the reference detector is a PbS detector.

9. The spectrometer of claim 1, wherein the beam splitter is a "Polka-dot" beam splitter and the reference detector is a PbS detector.

10. The spectrometer of claim 1, wherein the sample detector is a PbS detector.

11. The spectrometer of claim 1, wherein the software comprising a software routine written in a program that automatically corrects the wavelength scale of the instrument.

12. The spectrometer of claim 1, wherein the software comprising a software routine written in a program that automatically corrects the wavelength scale of the instrument from the positions of the 632.8 nm laser line in a spectrum.

13. A method for improving the calibration capabilities of a NIR spectrometer comprising:

providing a composite beam including a polychromatic radiation source beam that includes near infrared radiation, which has been wavelength dispersed and a known monochromatic reference wavelength beam;

splitting the composite beam such that at least some of the polychromatic beam passes through a sample container to a signal emitting sample detector and at least some of the reference beam passes to a signal emitting reference detector; and calibrating the signals from the sample detector with the referenced detector so they accurately reflect the true wavelengths of the polychromatic light absorbed by the sample in the sample container.

14. The method of claim 13, further comprising:

obtaining a He—Ne low power laser;

placing said laser at right angles to a source beam of the spectrometer where the He—Ne laser emits a collimated beam with a wavelength of 632.8 nm.;

obtaining a folding mirror; redirecting the low power collimated He—Ne laser beam with said mirror so that said folding mirror does not block the source beam from a quartz halogen lamp of the spectrometer and said laser beam at 632.8 nm is parallel to said source beam;

obtaining a "Polka-dot" beam splitter; diverting the majority of the laser beam with said "Polka-dot" beam splitter toward a PbS reference detector;

obtaining a PbS sample detector; positioning said PbS sample detector such that the source beam light strikes it after passing through a sample cell holder;

obtaining and installing a software routine written in a software program that automatically corrects the wavelength scale of the spectrometer from the position of 632.8 nm laser line in a spectrum.

* * * * *